United States Patent [19]

Koloff

[11] Patent Number: 4,521,411

[45] Date of Patent: Jun. 4, 1985

[54] ANALGESIC COMPOSITION

[76] Inventor: Theodora Koloff, 248 Nine Mile Rd., Ferndale, Mich. 48220

[21] Appl. No.: 548,659

[22] Filed: Nov. 4, 1983

[51] Int. Cl.$^3$ ............................................. A61K 35/78
[52] U.S. Cl. ................................................. 424/195.1
[58] Field of Search ......................................... 424/195

[56] References Cited

U.S. PATENT DOCUMENTS

| | | | |
|---|---|---|---|
| 812,554 | 2/1906 | Einhorn . | |
| 1,396,913 | 11/1921 | Bader . | |
| 1,550,350 | 8/1925 | Eisleb . | |
| 2,004,891 | 6/1935 | Goldberg | 167/52 |
| 2,139,818 | 12/1938 | Goldberg | 167/52 |
| 2,193,165 | 3/1940 | Curtis | 260/472 |
| 2,352,691 | 7/1944 | Curtis | 260/472 |
| 2,620,350 | 12/1952 | Beatty, III | 260/472 |
| 2,726,259 | 12/1955 | Simonoff | 260/472 |

OTHER PUBLICATIONS

Conn, Current Therapy (1970), p. 553.

*Primary Examiner*—Stanley J. Friedman
*Attorney, Agent, or Firm*—Gifford, VanOphem, Sheridan, Sprinkle & Nabozny

[57] ABSTRACT

An externally applicable analgesic composition comprises an extract derived from sumac leaves, sassafrass root, oak tree bark and an alcohol component, combined with benzocaine, procaine and menthol components. The topical application of this composition has proven effective for the temporary relief of pain and stiffness associated with arthritis, bursitis, muscle cramp and other aches and pains.

3 Claims, No Drawings

ANALGESIC COMPOSITION

BACKGROUND OF THE INVENTION

I. Field of the Invention

The present invention is directed to an analgesic composition, and more particularly to an externally applicable analgesic composition for relieving the pain and stiffness associated with arthritis, rheumatism, sprains, muscle cramps and the like.

II. Description of the Prior Art

Various compositions for the relief of pain have long been known. One class of these compositions is the analgesics. Analgesics can generally be considered compositions which have the effect of reducing or eliminating pain, while not effecting the senses or consciousness of the user. Typically used analgesics are aspirin (acetylsalicylic acid) and acetaminophen (N-acetyl-p-aminophenol).

However, as is well known to sufferers of arthritis, rheumatism, bursitis and other afflictions, a medically safe dose of many of the analgesics does not give the sufferer the desired relief. Of course, the problems and drawbacks of aspirin or acetominaphen overdose are well known. Excessive aspirin use may result in stomach upset and ulceration, while acetaminophen is not an anti-inflammatory agent. Expecially with continued use, there is a significant danger of overdose from the ingestion of such analgesics, because of the desire of the user to increase the dosage until relief is obtained.

A class of compounds which can provide a greater degree of relief from pain is the anesthetics, which induce a partial or total loss of sensation (the local or general anesthetics, respectively) or consciousness. This loss of sensation renders the user insensitive to pain. Typical anesthetics include the narcotics (sleep inducing agents which dull the senses) and the barbiturates. Typical narcotics are alkaloids such as morphine, codeine (morphine, phenolic methyl ether) and cocaine (methylbenzoylecgonine), and their derivatives. Typical local anesthetics are p-aminobenzoic acid derivatives, such as procaine (diethyl amino-ethyl ester) and benzocaine (diethyl ester).

Because of the strength or addictiveness of anesthetics, their use is often avoided for the relief of pains which are considered by some to be relatively minor and not incapacitating. Such pain can arise from typical ailments such as arthritis, rheumatism, rheumatoid arthritis, bursitis and the like. Although milder pain relievers, such as aspirin or acetaminophen, are usually prescribed for such pains, the safe dosage strength may not be sufficient to meet the pain.

SUMMARY OF THE PRESENT INVENTION

The present invention overcomes these and other problems by providing an externally applicable analgesic composition which relieves pain, soreness and swelling in both shallow and deep body tissues. The composition comprises an alcohol extract derived from an herb combination of sumac leaves, sassafrass root and oak tree bark; and also comprises benzocaine, procaine hydrochloride and menthol. The composition is prepared by first extracting the alcohol-extractable constituents from the herbs by an alcohol component, such as 70 percent wine spirits; mixing benzocaine, procaine hydrochloride and menthol (methyl hydroxyisopropylcyclohexane) with this extract; and filtering the mixture. This particular combination of ingredients results in an externally applicable analgesic composition which relieves pain from injury or disease, in both shallow and deep body tissues, yet which avoids a complete numbing of the area in question and avoids any deleterious effects on the sobriety of the user.

DETAILED DESCRIPTION OF A PREFERRED EMBODIMENT OF THE PRESENT INVENTION

A determination is first made of the volume of composition that is desired to be produced. The ingredients below are combined in the proportions indicated, the actual amounts varying according to the volume of alcohol component initially employed.

The alcohol component can be any alcohol or solution thereof which is safe for application to the human body. 70% isopropyl alcohol, rubbing alcohol or ethanol is preferred, and 70% wine spirits is particularly preferred.

Sumac leaves, sassafrass root and oak tree bark are added to a quantity of about one gallon of alcohol component. The purpose of adding these herbs is to permit the extraction of the alcohol-component-extractable constituents from the herbs (the "herb strength" referred to in folk medicine). The residue after such extraction will be discarded before, or preferably after, addition of components containing benzocaine, procaine and menthol.

Preferably, these herbs are ground or shredded to increase the efficiency of the extraction. To the gallon of alcohol component, about 100 grams of sumac leaves, about 90 grams of sassafras root, and about 150 grams of oak tree bark are added. The preferred variety of sumac is the European variety, *C. Cotinus*, and the sassafras root is also preferably of the European variety. Other varieties of sumac (*Rhus cotinus* and *Rhus continus L.*) and sassafras (*Sassafrass variifolium, Sassafras sassafras, Sassafras officinale,* and *Laurus sassafras*) do or are expected to perform equally as well in the present invention.

This mixture of herbs and alcohol component is then allowed to stand in sealed, nonreactive container as long as possible, in any event for at least two to three weeks. Of course, other extraction methods, such as countercurrent extraction, are useful as well, so long as they permit as complete as possible the extraction of the extractable herb constituents. After such extraction, the alcohol component (containing the extractable herb constituents) comprises the extract portion of the analgesic composition of the present invention.

After preparation of the extract portion, components containing benzocaine, procaine (preferably in the form of procaine hydrochloride or another acid salt of procaine) and menthol are added to the extract. About 50 grams of benzocaine component, about 50 grams of procaine hydrochloride component and about 125 grams of menthol component are added to the gallon of extract. Optimally, the benzocaine component is Anaesthesin, and the procaine hydrochloride component is Novocain. Anaesthesin and Novocain are registered trademarks of Winthrop Laboratories, a division of Sterling Drug Company, New York, New York, for its benzocaine and procaine hydrochloric products. Also preferably, the menthol component comprises pure l-menthol, the levorotatory isomer of menthol. l-menthol is known to be a white, crystalline solid at room temperature, having a melting point of about 44° centigrade. The d and dl isomers of menthol are expected to be useful as well, the dl form being known to be a congealed solid at room temperature, having a melting point of about 27°–28° centigrade.

In accordance with general chemical principles, the materials should be added in the order of decreasing resistance to dissolution (i.e., increasing solubility). Thus, it is preferable to add the menthol component to the extract after the addition and dissolution of the benzocaine and procaine hydrochloride components. After the addition and mixing of these components with the extract portion, the bottle is again sealed. Preparation of the analgesic composition is now complete. The nonalcohol-component-extractable herb constituents (herb residue) will settle to the bottom of the container quickly.

The composition can then be filtered and transferred to a more convenient container, or separated from the residue by decantation or by any other known separation method.

Use of the analgesic composition according to the present invention is straightforward. The composition is externally or topically applied to the painful area of the body, in the same fashion as a liniment. Use in this fashion, the composition has proven useful against the pains associated with arthritis, rheumatism, rheumatoid arthritis, bursitis, sprains, muscle strain and tension, itching, weed poisoning (such as poison ivy), sore throat, surgery (especially surgical scars), headache, stomach ache and muscle cramps, among other ailments.

This preferred embodiment of the present invention is illustrated by the following example:

EXAMPLE 100 grams of shredded sumac leaves (*C. Cotinus*), 90 grams of ground sassafras root and 150 grams of ground oak tree bark are placed in a gallon bottle. The bottle is filled with 70% wine spirits. The mixture of herbs and wine spirits is then allowed to stand for three weeks.

After this period of time, 50 grams of Anaesthesin and 50 grams of Novocain are mixed with the wine spirits and herb mixture, this mixture being stirred with a wooden spoon until the Anaesthesin and Novacain are fully dissolved. 125 grams of l-menthol are subsequently added with stirring, until it is also fully dissolved.

After such mixing, the bottle is closed tightly to permit the herb residue (the nonextractable herb constituents) to settle. The analgesic composition so formed is then filtered and transferred to smaller bottles for use.

In use, the composition is applied topically to the desired area of the body in the same fashion as a liniment. The composition has been described by its users as giving almost immediate relief to the stiffness of joints affected by rheumatoid arthritis, such relief lasting two or three hours. Repeated treatment (three to four times daily, for a period of two to four weeks) has been described by users as relieving the stiffness and pain of bursitis by 80%, along with an improvement in the muscular strength of the user.

Thus, the particular combination of ingredients provided herein results in an externally applicable analgesic composition, one which provides relief from pain without affecting the sobriety of the user. Having described my invention, however, many modifications thereto will become apparent to those skilled in the art to which it pertains without deviation from the spirit of the invention as defined by the scope of the appended claims.

I claim:

1. A process for making a topical analgesic composition, comprising the steps of:
    (a) forming an extract by mixing about 100 grams of ground or shredded *cotinus* leaves, about 90 grams of ground or shredded sassafras root, and about 150 grams of ground or shredded oak tree bark, with about one gallon of 70 percent wine spirit alcohol;
    (b) allowing the admixture step (a) to stand for at least two weeks;
    (c) dissolving about 50 grams benzocain, an amount of a procaine component containing an amount of procaine equivalent to about 50 grams of procaine hydrochloride, and about 50 grams menthol, in that order in said extract; and
    (d) separating said extract by filtering the product of step (c).

2. The product of the process according to claim 1.

3. A method of effecting topical analgesia in body tissues comprising the administration of an effective amount of the product of claim 2 to said tissues.

* * * * *

UNITED STATES PATENT AND TRADEMARK OFFICE
CERTIFICATE OF CORRECTION

PATENT NO. : 4,521,411
DATED : June 4, 1985
INVENTOR(S) : THEODORA KOLOFF

It is certified that error appears in the above-identified patent and that said Letters Patent is hereby corrected as shown below:

Column 4, line 36, before "grams menthol" delete "50" and insert --125--.

Signed and Sealed this

Eleventh Day of November, 1986

Attest:

DONALD J. QUIGG

Attesting Officer     Commissioner of Patents and Trademarks